(12) United States Patent
Chang

(10) Patent No.: US 8,128,594 B1
(45) Date of Patent: Mar. 6, 2012

(54) SAFETY SYRINGE

(76) Inventor: Li-Feng Chang, Xindian (TW)

( * ) Notice: Subject to any disclaimer, the term of this patent is extended or adjusted under 35 U.S.C. 154(b) by 0 days.

(21) Appl. No.: 12/938,497

(22) Filed: Nov. 3, 2010

(51) Int. Cl.
*A61M 5/00* (2006.01)

(52) U.S. Cl. .................................................. 604/110

(58) Field of Classification Search ............... 604/110
See application file for complete search history.

(56) References Cited

U.S. PATENT DOCUMENTS

| | | | | |
|---|---|---|---|---|
| 4,801,295 A * | 1/1989 | Spencer | | 604/198 |
| 4,923,447 A * | 5/1990 | Morgan | | 604/198 |
| 5,318,537 A * | 6/1994 | Van Der Merwe | | 604/110 |
| 5,324,264 A * | 6/1994 | Whitaker | | 604/110 |
| 5,383,857 A * | 1/1995 | Levitov | | 604/110 |
| 5,403,286 A * | 4/1995 | Lockwood, Jr. | | 604/110 |
| 5,403,288 A * | 4/1995 | Stanners | | 604/232 |
| 5,405,326 A * | 4/1995 | Haber et al. | | 604/110 |
| 5,423,758 A * | 6/1995 | Shaw | | 604/110 |
| 5,429,612 A * | 7/1995 | Berthier | | 604/198 |
| 5,445,620 A * | 8/1995 | Haber et al. | | 604/232 |
| 5,562,624 A * | 10/1996 | Righi et al. | | 604/110 |
| 5,595,566 A * | 1/1997 | Vallelunga et al. | | 604/197 |
| 5,695,475 A * | 12/1997 | Best et al. | | 604/198 |
| 6,013,059 A * | 1/2000 | Jacobs | | 604/198 |
| 6,083,199 A * | 7/2000 | Thorley et al. | | 604/110 |
| 6,093,170 A * | 7/2000 | Hsu et al. | | 604/110 |
| RE37,439 E * | 11/2001 | Firth et al. | | 604/110 |
| 6,319,234 B1 * | 11/2001 | Restelli et al. | | 604/198 |
| 6,562,003 B2 * | 5/2003 | Koch et al. | | 604/110 |
| 6,575,939 B1 * | 6/2003 | Brunel | | 604/187 |
| 6,616,631 B2 * | 9/2003 | Takagi et al. | | 604/110 |
| 6,676,638 B2 * | 1/2004 | Takagi et al. | | 604/167.03 |
| 6,679,864 B2 * | 1/2004 | Gagnieux et al. | | 604/198 |
| 6,926,698 B2 * | 8/2005 | Lin | | 604/198 |
| 7,282,042 B2 * | 10/2007 | Wang | | 604/110 |
| 7,500,967 B2 * | 3/2009 | Thorley et al. | | 604/218 |
| 7,740,610 B2 * | 6/2010 | Moh et al. | | 604/110 |
| 7,806,859 B2 * | 10/2010 | Lee et al. | | 604/110 |
| 7,824,379 B2 * | 11/2010 | Doyle | | 604/198 |
| 8,048,029 B2 * | 11/2011 | Gillespie et al. | | 604/110 |
| 2004/0116853 A1 * | 6/2004 | Halseth et al. | | 604/110 |
| 2004/0230158 A1 * | 11/2004 | Malenchek | | 604/110 |
| 2005/0165353 A1 * | 7/2005 | Pessin | | 604/110 |
| 2006/0189933 A1 * | 8/2006 | Alheidt et al. | | 604/110 |
| 2006/0264825 A1 * | 11/2006 | Westbye et al. | | 604/110 |
| 2007/0073219 A1 * | 3/2007 | Yang | | 604/110 |
| 2007/0078408 A1 * | 4/2007 | Wang | | 604/198 |
| 2007/0129674 A1 * | 6/2007 | Liversidge | | 604/110 |
| 2007/0129677 A1 * | 6/2007 | Lin | | 604/110 |
| 2007/0232998 A1 * | 10/2007 | Yang et al. | | 604/110 |
| 2011/0137246 A1 * | 6/2011 | Cali et al. | | 604/110 |

* cited by examiner

*Primary Examiner* — Nicholas Lucchesi
*Assistant Examiner* — Victoria P Campbell
(74) *Attorney, Agent, or Firm* — Alan Kamrath; Kamrath IP Lawfirm, PA

(57) ABSTRACT

A safety syringe includes a barrel, an inner tube movably mounted in the barrel, and an elastic member mounted on the barrel and connected with the inner tube to pull the inner tube outward relative to the barrel. Thus, the elastic member is made of plastic or rubber material to largely decrease the cost of fabrication of the safety syringe.

14 Claims, 8 Drawing Sheets

SAFETY SYRINGE

BACKGROUND OF THE INVENTION

1. Field of the Invention

The present invention relates to a syringe and, more particularly, to a disposable safety syringe that can be disposed of and thrown away.

2. Description of the Related Art

A conventional safety syringe comprises a barrel, an inner tube mounted in the barrel and provided with a needle, a spring mounted on the inner tube and biased between the inner tube and the barrel, and a plunger movably mounted in the inner tube. However, the spring is made of metal to largely increase the cost of fabrication of the safety syringe. In addition, a user has to user his/her two hands to hold the barrel and to operate the spring so as to pull the inner tube from the barrel and to retract and hide the needle, thereby greatly causing inconvenience to the user.

BRIEF SUMMARY OF THE INVENTION

In accordance with the present invention, there is provided a safety syringe, comprising a barrel, an inner tube movably mounted in the barrel, and an elastic member mounted on the barrel and connected with the inner tube to pull the inner tube outward relative to the barrel.

The barrel has an inner wall provided with a through hole. The barrel has a peripheral wall provided with two opposite guide tracks. Each of the two guide tracks of the barrel includes a sliding slot, an anti-reverse channel connected to the sliding slot, and a flexible guide ramp located at a connection between the sliding slot and the anti-reverse channel. The anti-reverse channel of each of the two guide tracks has an end provided with an anti-reverse block. The barrel has an end portion provided with two opposite fixing posts and a flexible locking hook.

The inner tube has a first end inserted into the through hole of the barrel and provided with a needle hub for mounting a needle. The inner tube has a second end protruding outward from the through hole of the barrel and provided with a perforated locking plate selectively snapped onto the locking hook of the barrel. The inner tube has a peripheral wall provided with two opposite guide rods slidable in the two guide tracks of the barrel respectively.

The elastic member is received in the through hole of the barrel and has a middle portion provided with a locking ring locked onto the needle hub of the inner tube. The elastic member has two opposite extension legs extending from the locking ring respectively. Each of the two extension legs of the elastic member has a free end provided with a fixing hole fixed on a respective one of the two fixing posts of the barrel to lock each of the two extension legs of the elastic member onto the barrel.

The primary objective of the present invention is to provide a safety syringe having a lower cost of fabrication.

Another objective of the present invention is to provide a safety syringe that can be operated by a user's one hand.

Further benefits and advantages of the present invention will become apparent after a careful reading of the detailed description with appropriate reference to the accompanying drawings.

BRIEF DESCRIPTION OF THE SEVERAL VIEWS OF THE DRAWING(S)

DETAILED DESCRIPTION OF THE INVENTION

Figure 1:
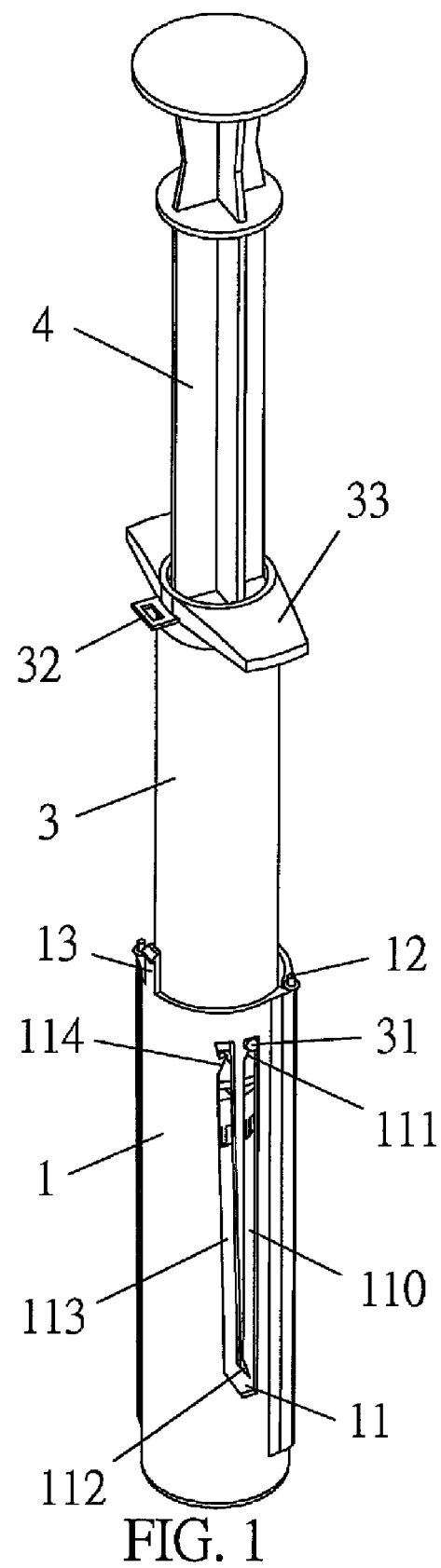
FIG. 1 is a perspective view of a safety syringe in accordance with the preferred embodiment of the present invention.
Figure 2:
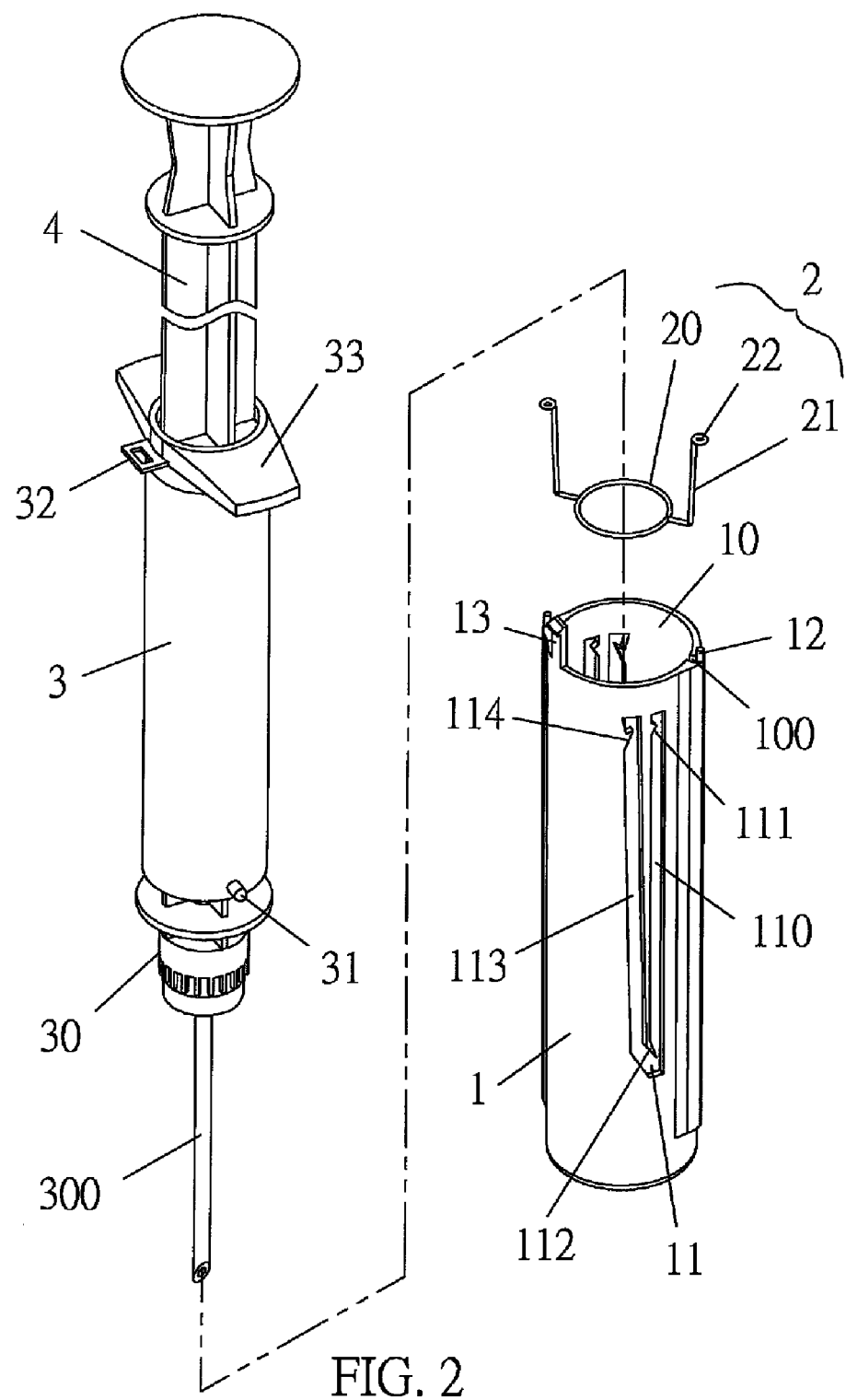
FIG. 2 is an exploded perspective view of the safety syringe as shown in FIG. 1.
Figure 3:
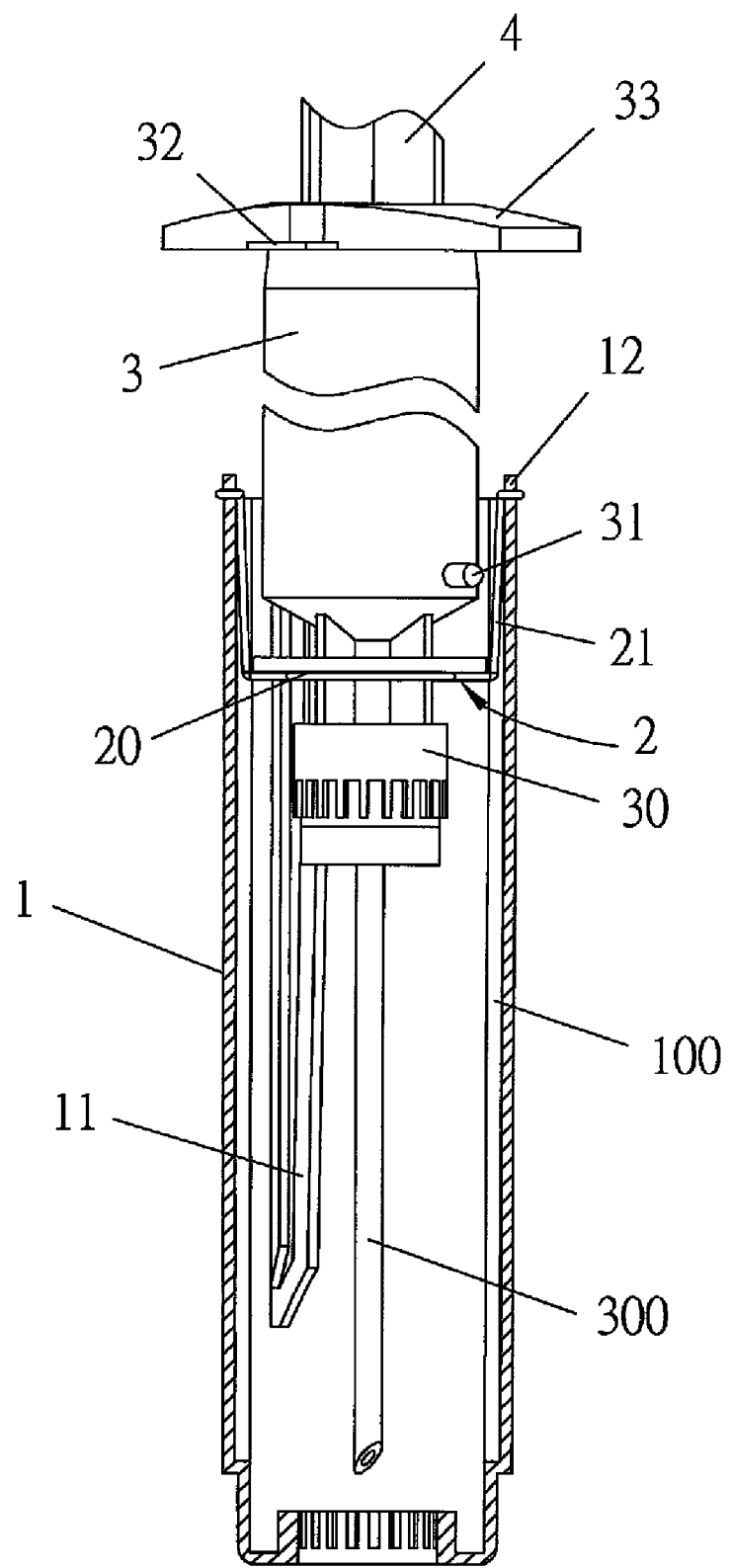
FIG. 3 is a front cross-sectional view of the safety syringe as shown in FIG. 1.

Referring to the drawings and initially to FIGS. 1-3, a safety syringe in accordance with the preferred embodiment of the present invention comprises a barrel 1, an inner tube 3 movably mounted in the barrel 1, and an elastic member 2 mounted on the barrel 1 and connected with the inner tube 3 to pull the inner tube 3 outward relative to the barrel 1. The safety syringe further comprises a plunger 4 movably mounted in the inner tube 3.

The barrel 1 has an inner wall provided with a through hole 10. The barrel 1 has a peripheral wall provided with two opposite guide tracks 11. Each of the two guide tracks 11 of the barrel 1 is connected to the through hole 10 and includes a sliding slot 110, an anti-reverse channel 113 connected to the sliding slot 110, and a flexible guide ramp 112 located at a connection between the sliding slot 110 and the anti-reverse channel 113. The sliding slot 110 and the anti-reverse channel 113 of each of the two guide tracks 11 are parallel with each other. The anti-reverse channel 113 of each of the two guide tracks 11 has an end provided with an anti-reverse block 114. The sliding slot 110 of each of the two guide tracks 11 has an end provided with a stop block 111. The barrel 1 has an end portion provided with two opposite fixing posts 12 and a flexible locking hook 13. The two fixing posts 12 and the locking hook 13 of the barrel 1 are located at a rim of the through hole 10. The inner wall of the barrel 1 has a surface provided with two opposite guide grooves 100. Each of the two guide grooves 100 of the barrel 1 is connected to the through hole 10.

The inner tube 3 has a first end inserted into the through hole 10 of the barrel 1 and provided with a needle hub 30 for mounting a needle 300. The inner tube 3 has a second end protruding outward from the through hole 10 of the barrel 1 and provided with a perforated locking plate 32 selectively snapped onto the locking hook 13 of the barrel 1. The inner tube 3 has a peripheral wall provided with two opposite guide rods 31 slidable in the two guide tracks 11 of the barrel 1 respectively. The two guide rods 31 of the inner tube 3 are located beside the needle hub 30. Each of the two guide rods 31 of the inner tube 3 is movable in the sliding slot 110 and the anti-reverse channel 113 of the respective guide track 11 and is movable from the sliding slot 110 through the guide ramp 112 into the anti-reverse channel 113 of the respective guide track 11. Each of the two guide rods 31 of the inner tube 3 is selectively locked by the stop block 111 of the sliding slot 110 of the respective guide track 11 or the anti-reverse block 114 of the anti-reverse channel 113 of the respective guide track 11. The second end of the inner tube 3 is provided with a stop flange 33 that is movable to abut the barrel 1 to prevent the inner tube 3 from extending into the barrel 1 completely. The stop flange 33 of the inner tube 3 is located beside the locking plate 32.

The elastic member 2 is made of plastic or rubber material. The elastic member 2 is received in the through hole 10 of the barrel 1 and has a middle portion provided with a locking ring 20 locked onto the needle hub 30 of the inner tube 3 so that the locking ring 20 of the elastic member 2 is movable in concert with the needle hub 30 of the inner tube 3. The elastic member 2 has two opposite extension legs 21 extending from the locking ring 20 respectively. Each of the two extension legs 21 of the elastic member 2 has a free end provided with a fixing hole 22 fixed on a respective one of the two fixing posts 12 of the barrel 1 to lock each of the two extension legs 21 of the elastic member 2 onto the barrel 1 so that the elastic member 2 is extendable by movement of the inner tube 3 when the inner tube 3 is movable relative to the barrel 1. Each of the two extension legs 21 of the elastic member 2 is limited in and guided by a respective one of the two guide grooves 100 of the barrel 1.

Figure 4:
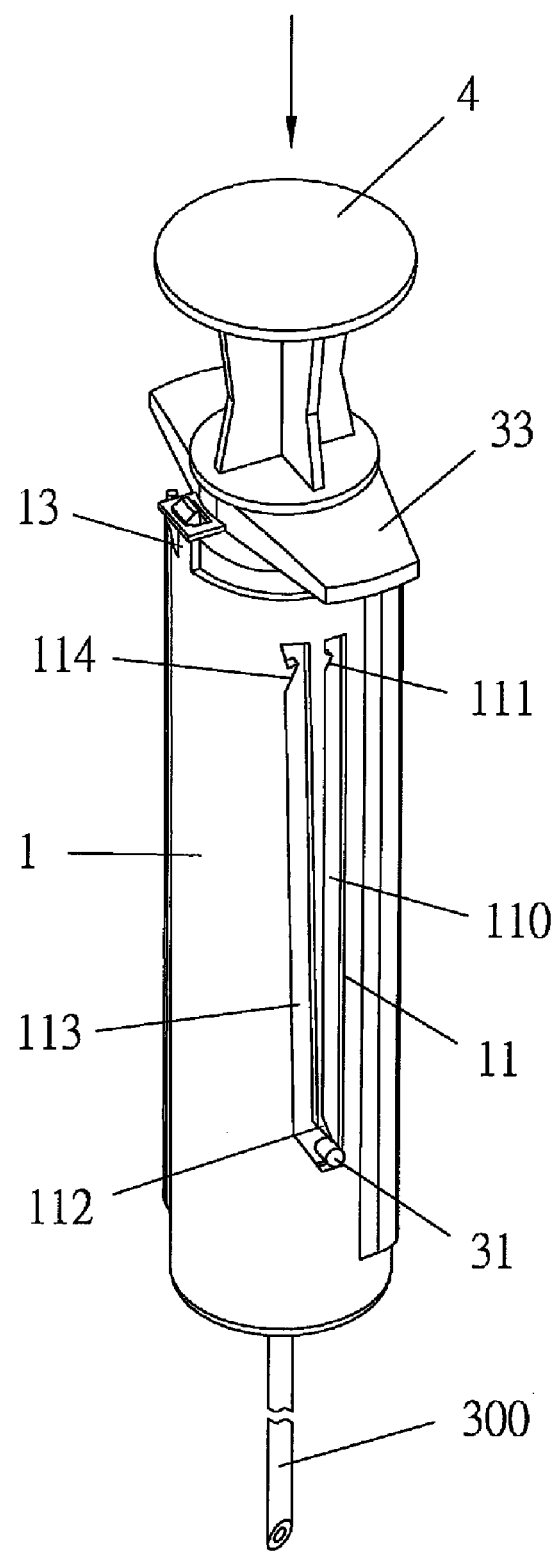
FIG. 4 is a schematic operational view of the safety syringe as shown in FIG. 1.

In operation, referring to FIGS. 3 and 4 with reference to FIGS. 1 and 2, the inner tube 3 initially projects outward from the barrel 1 as shown in FIG. 1. Then, the inner tube 3 is pushed and inserted into the through hole 10 of the barrel 1 so that each of the two guide rods 31 of the inner tube 3 is detached from the stop block 111 of the sliding slot 110 of the respective guide track 11 and is moved in the sliding slot 110 of the respective guide track 11. At this time, the locking ring 20 of the elastic member 2 is locked onto the needle hub 30 of the inner tube 3 to move in concert with the inner tube 3, and the fixing hole 22 of each of the two extension legs 21 of the elastic member 2 is fixed on the respective fixing post 12 of the barrel 1 so that the elastic member 2 is extended and tensioned by movement of the inner tube 3 when the inner tube 3 is moved toward the barrel 1. When the stop flange 33 of the inner tube 3 is moved to abut the barrel 1, the locking plate 32 of the inner tube 3 is snapped onto the locking hook 13 of the barrel 1 to lock the inner tube 3 onto the barrel 1 temporarily as shown in FIG. 4. At this time, each of the two guide rods 31 of the inner tube 3 is moved from the sliding slot 110 to the guide ramp 112 of the respective guide track 11. When the inner tube 3 is fully inserted into the through hole 10 of the barrel 1, the needle 300 of the inner tube 3 projects outward from the barrel 1 for use with a user.

Figure 5:
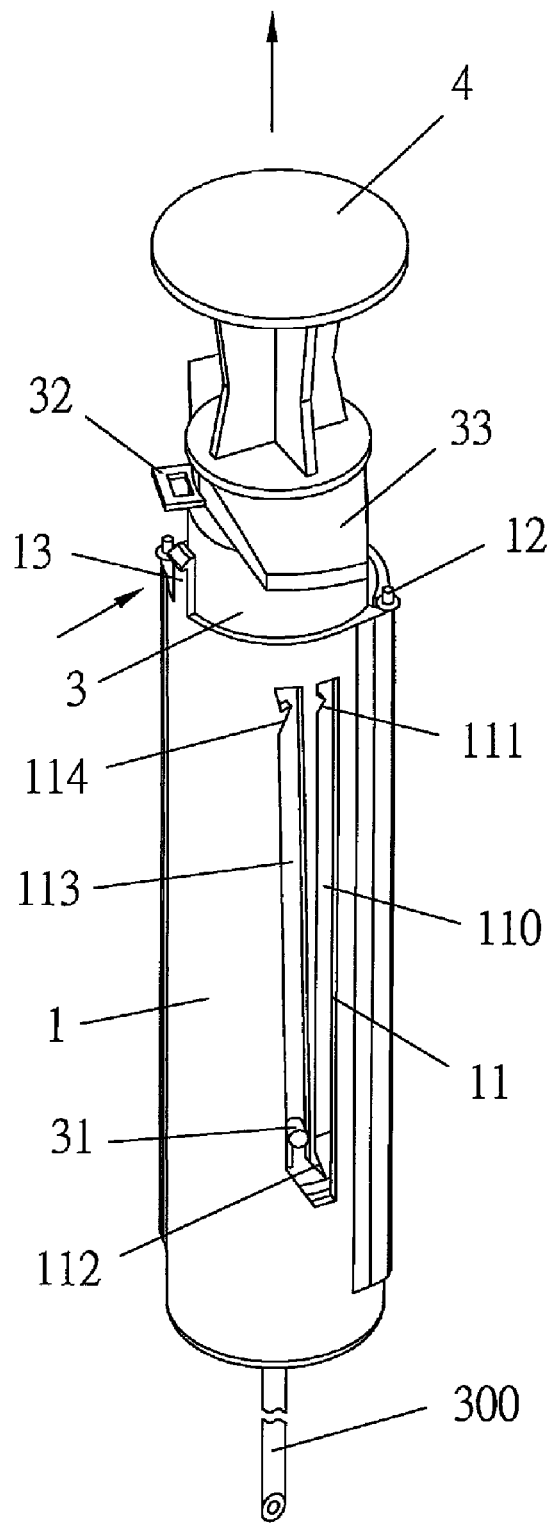
FIG. 5 is a schematic operational view of the safety syringe as shown in FIG. 4.

As shown in FIG. 5, when the locking plate 32 of the inner tube 3 is detached from the locking hook 13 of the barrel 1 to unlock the inner tube 3 from the barrel 1, the inner tube 3 is pulled outward by the restoring force of the elastic member 2 so that the inner tube 3 is moved outward relative to the barrel 1. At this time, each of the two guide rods 31 of the inner tube 3 is moved from the guide ramp 112 into the anti-reverse channel 113 of the respective guide track 11 and is moved in the anti-reverse channel 113 of the respective guide track 11.

Figure 6:
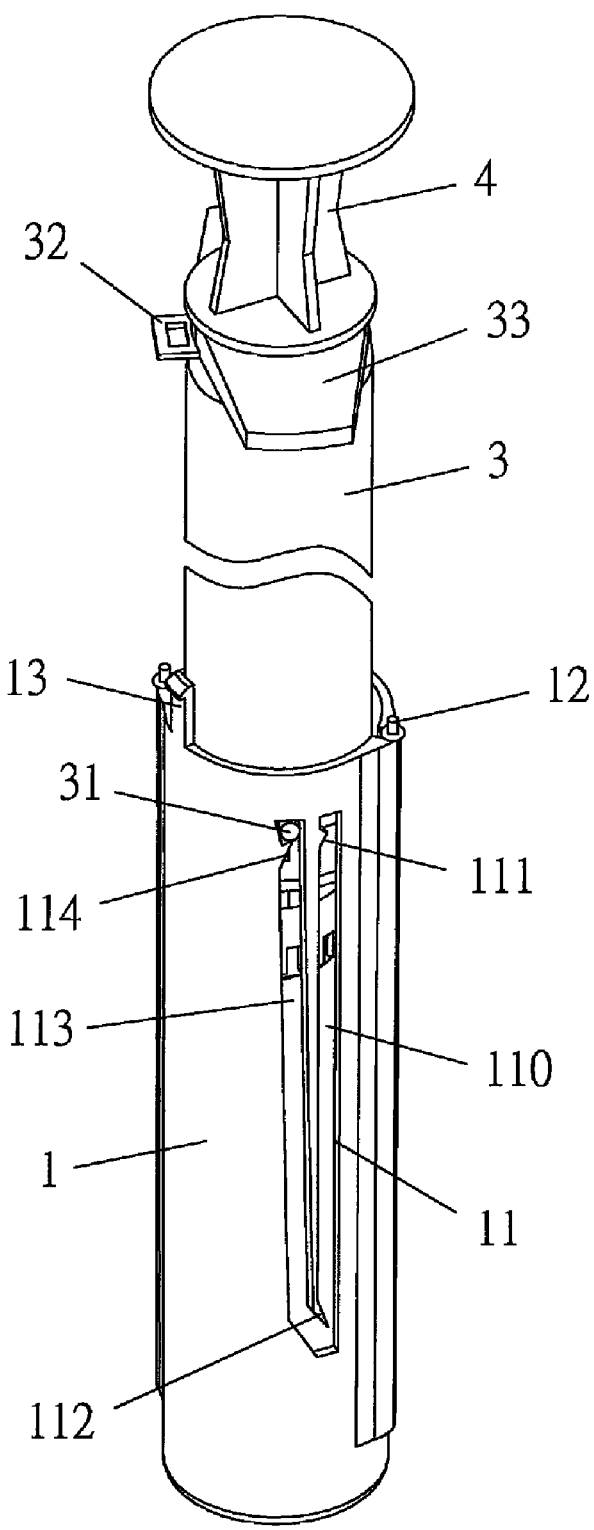
FIG. 6 is a schematic operational view of the safety syringe as shown in FIG. 5.

As shown in FIG. 6, when each of the two guide rods 31 of the inner tube 3 is moved upward in the anti-reverse channel 113 of the respective guide track 11 and is locked by the anti-reverse block 114 of the anti-reverse channel 113 of the respective guide track 11, the inner tube 3 is locked onto the barrel 1 so that the inner tube 3 cannot be moved relative to and inserted into the barrel 1 again. At this time, the needle 300 of the inner tube 3 is retracted into the barrel 1 to protect the user's safety.

Figure 7:
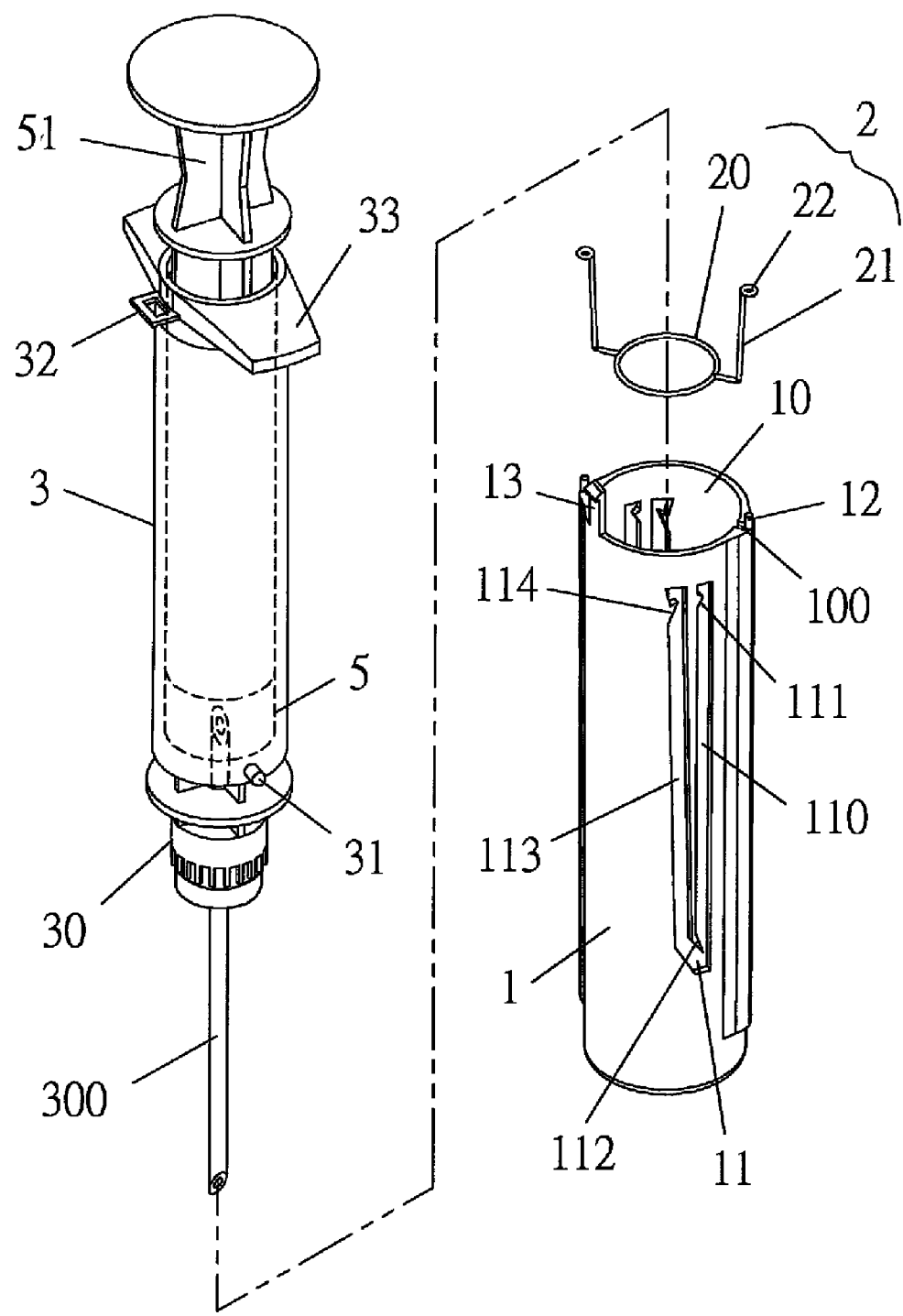
FIG. 7 is an exploded perspective view of a safety syringe in accordance with another preferred embodiment of the present invention.

Referring to FIG. 7, the plunger 4 is undefined, and the safety syringe further comprises a cartridge 5 mounted in the inner tube 3 and connected to the needle 300 of the inner tube 3, and a pull handle 51 retractably mounted in the cartridge 5. The cartridge 5 can be used to store blood. Thus, when the pull handle 51 is pulled outward from the cartridge 5, the blood is drawn from the needle 300 of the inner tube 3 into the cartridge 5.

Figure 8:
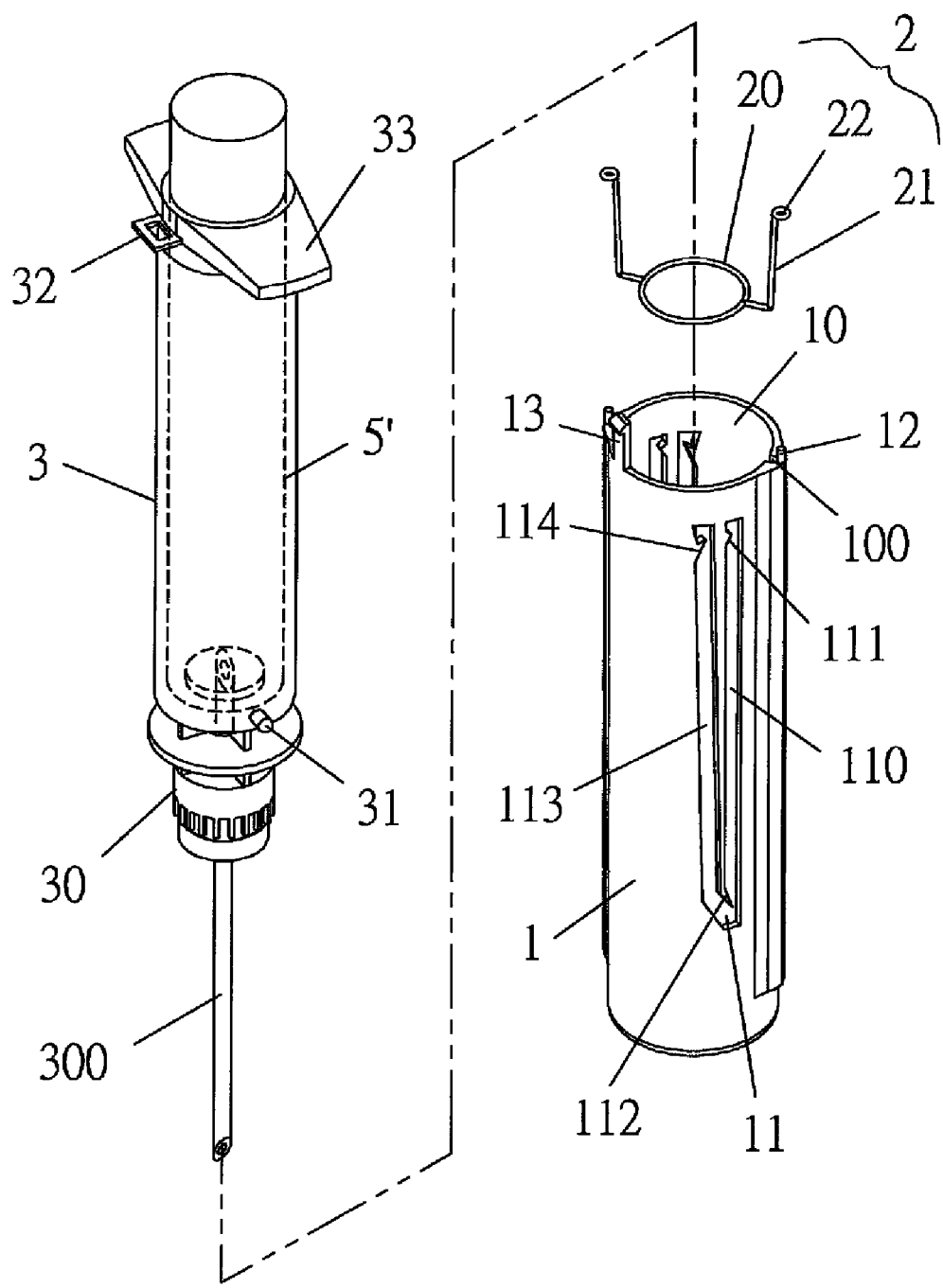
FIG. 8 is an exploded perspective view of a safety syringe in accordance with another preferred embodiment of the present invention.

Referring to FIG. 8, the cartridge 5' is a single bottle which is disposed at a vacuum state to produce a vacuum suction force to draw the blood from the needle 300 of the inner tube 3.

Accordingly, the elastic member 2 is made of plastic or rubber material to largely decrease the cost of fabrication of the safety syringe. In addition, after the locking plate 32 of the inner tube 3 is detached from the locking hook 13 of the barrel 1, the inner tube 3 is moved outward relative to the barrel 1 automatically by the restoring force of the elastic member 2 so as to retract the needle 300 of the inner tube 3 into the barrel 1, so that the user can detach the locking plate 32 of the inner tube 3 from the locking hook 13 of the barrel 1 by his/her one hand only, thereby facilitating the user retracting and hiding the needle 300. Further, the inner tube 3 can co-operate with a plunger 4 and a cartridge 5, thereby enhancing the versatility of the safety syringe.

Although the invention has been explained in relation to its preferred embodiment(s) as mentioned above, it is to be understood that many other possible modifications and variations can be made without departing from the scope of the present invention. It is, therefore, contemplated that the appended claim or claims will cover such modifications and variations that fall within the true scope of the invention.

The invention claimed is:

1. A safety syringe, comprising:
a barrel;
an inner tube movably mounted in the barrel; and
an elastic member mounted on the barrel and connected with the inner tube to pull the inner tube outward relative to the barrel;
wherein the barrel has an inner wall provided with a through hole;
the barrel has a peripheral wall provided with two opposite guide tracks;
each of the two guide tracks of the barrel includes a sliding slot, an anti-reverse channel connected to the sliding slot, and a flexible guide ramp located at a connection between the sliding slot and the anti-reverse channel;
the anti-reverse channel of each of the two guide tracks has an end provided with an anti-reverse block;
the barrel has an end portion provided with two opposite fixing posts and a flexible locking hook;
the inner tube has a first end inserted into the through hole of the barrel and provided with a needle hub for mounting a needle;
the inner tube has a second end protruding outward from the through hole of the barrel and provided with a perforated locking plate selectively snapped onto the locking hook of the barrel;
the inner tube has a peripheral wall provided with two opposite guide rods slidable in the two guide tracks of the barrel respectively;
the elastic member is received in the through hole of the barrel and has a middle portion provided with a locking ring locked onto the needle hub 5 of the inner tube;
the elastic member has two opposite extension legs extending from the locking ring respectively;
each of the two extension legs of the elastic member has a free end provided with a fixing hole fixed on a respective one of the two fixing posts of the barrel to lock each of the two extension legs of the elastic member onto the barrel; and the inner wall of the barrel has a surface provided with two opposite guide grooves;

each of the two extension legs of the elastic member is limited in and guided by a respective one of the two guide grooves of the barrel.

2. The safety syringe of claim 1, wherein the sliding slot of each of the two guide tracks has an end provided with a stop block;

each of the two guide rods of the inner tube is selectively locked by the stop block of the sliding slot of the respective guide track or the anti-reverse block of the anti-reverse channel of the respective guide track.

3. The safety syringe of claim 1, wherein the second end of the inner tube is provided with a stop flange that is movable to abut the barrel;

the stop flange of the inner tube is located beside the locking plate.

4. The safety syringe of claim 1, wherein the safety syringe further comprises a plunger movably mounted in the inner tube.

5. The safety syringe of claim 1, wherein the safety syringe further comprises a cartridge mounted in the inner tube and connected to the needle of the inner tube.

6. The safety syringe of claim 5, wherein the safety syringe further comprises a pull handle retractably mounted in the cartridge.

7. The safety syringe of claim 5, wherein the cartridge is a single bottle which is disposed at a vacuum state.

8. The safety syringe of claim 1, wherein the elastic member is made of plastic or rubber material.

9. The safety syringe of claim 1, wherein each of the two guide tracks of the barrel is connected to the through hole.

10. The safety syringe of claim 1, wherein the sliding slot and the anti-reverse channel of each of the two guide tracks are parallel with each other.

11. The safety syringe of claim 1, wherein the two fixing posts and the locking hook of the barrel are located at a rim of the through hole.

12. The safety syringe of claim 1, wherein each of the two guide grooves of the barrel is connected to the through hole.

13. The safety syringe of claim 1, wherein the two guide rods of the inner tube are located beside the needle hub.

14. The safety syringe of claim 1, wherein each of the two guide rods of the inner tube is movable in the sliding slot and the anti-reverse channel of the respective guide track and is movable from the sliding slot through the guide ramp into the anti-reverse channel of the respective guide track.

* * * * *